United States Patent [19]

Chadwick

[11] Patent Number: 5,395,568
[45] Date of Patent: Mar. 7, 1995

[54] FEEDBACK-CONTROLLED OXYGEN REGULATION SYSTEM FOR BENTHIC FLUX CHAMBERS AND METHOD FOR MAINTAINING A CONSTANT VOLUME OF OXYGEN THEREFOR

[75] Inventor: David B. Chadwick, San Diego, Calif.

[73] Assignee: The United States of America as represented by the Secretary of the Navy, Washington, D.C.

[21] Appl. No.: 161,948

[22] Filed: Dec. 3, 1993

[51] Int. Cl.⁶ .............................................. B01F 3/04
[52] U.S. Cl. ................................ 261/36.1; 261/122.1
[58] Field of Search .................. 261/122.1, 121.1, 36.1

[56] References Cited

U.S. PATENT DOCUMENTS

| | | | |
|---|---|---|---|
| 3,199,070 | 8/1965 | Baier, Jr. | 340/5 |
| 3,320,928 | 5/1967 | Smith | 261/121.1 |
| 3,552,726 | 1/1971 | Kraft | 261/121.1 |
| 3,572,550 | 3/1971 | Colomina et al. | 261/121.1 |
| 3,731,522 | 5/1973 | Mikesell | 261/122.1 |
| 3,845,303 | 10/1974 | Richards et al. | 250/303 |
| 3,925,522 | 12/1975 | Schreiber | 261/121.1 |
| 3,987,677 | 10/1976 | Alter | 73/421.5 R |
| 4,089,209 | 5/1978 | Grana et al. | 73/61 R |
| 4,166,392 | 9/1979 | Farnworth | 73/425.4 R |
| 4,187,390 | 2/1980 | Gore | 261/104 |
| 4,251,365 | 2/1981 | Speece | 261/121.1 |
| 4,287,062 | 9/1981 | Nordenskjold | 261/121.1 |
| 4,301,007 | 11/1981 | Savard et al. | 261/121.1 |
| 4,762,009 | 8/1988 | Scrudto | 73/863.52 |
| 5,062,309 | 11/1991 | Voll et al. | 73/864.44 |
| 5,085,085 | 2/1992 | Anderson | 73/863.02 |
| 5,167,802 | 12/1992 | Sandstrom et al. | 210/134 |
| 5,172,332 | 12/1992 | Hungerford et al. | 364/510 |
| 5,230,838 | 7/1993 | Oaki et al. | 261/121.1 |

Primary Examiner—Tim Miles
Attorney, Agent, or Firm—Harvey Fendelman; Thomas Glenn Keough

[57] ABSTRACT

A method and apparatus for maintaining oxygen levels in an isolated volume of fluid (e.g. water) is provided. The method and apparatus are adaptable for use with a benthic flux sampling device and rely upon periodically measuring the oxygen concentration in the isolated volume with an oxygen sensor system, monitoring the oxygen sensor system with a control unit, and automatically dispensing oxygen into the isolated volume of fluid with an oxygenation system to maintain a predetermined constant level of oxygenation that corresponds to the ambient.

22 Claims, 11 Drawing Sheets

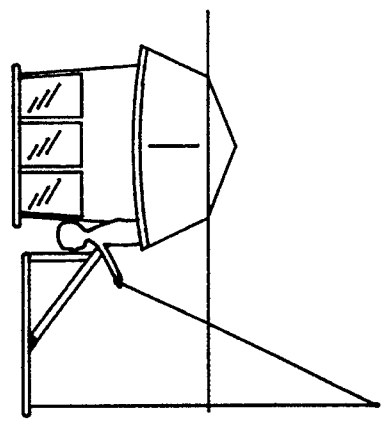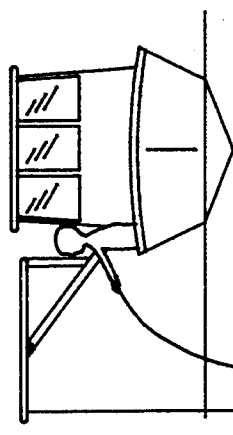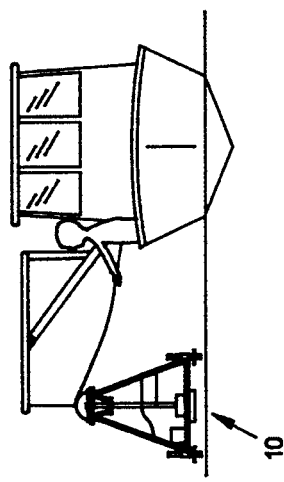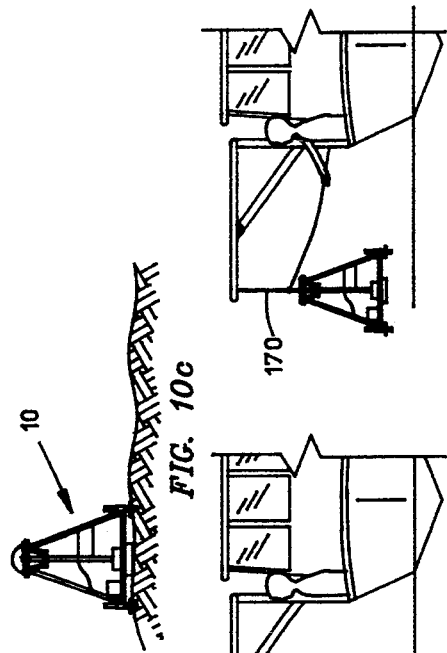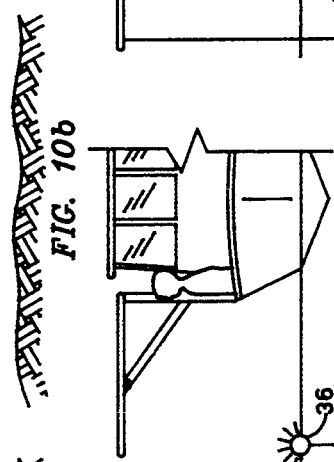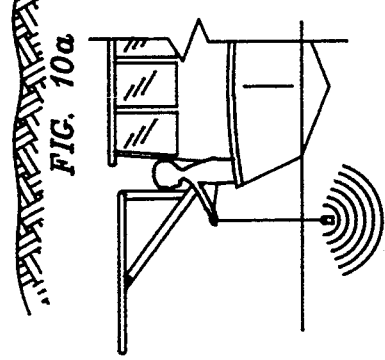

FEEDBACK-CONTROLLED OXYGEN REGULATION SYSTEM FOR BENTHIC FLUX CHAMBERS AND METHOD FOR MAINTAINING A CONSTANT VOLUME OF OXYGEN THEREFOR

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

This invention relates generally to fluid sampling and more particularly to maintaining oxygen concentrations in a sample of water during benthic flux rate sampling.

Sediment in many bays, harbors and coastal waters is contaminated with metal and organic toxins. These toxins are known to cause extensive biological harm to aquatic environments. As a result of the threat of biological harm, remedies for contamination due to toxins are continually being devised.

In order to effectuate a satisfactory remedy however, the source of contamination must be identified. The remedial urgency (i.e. biological risk) relative to other contaminated sites must also be determined. With toxin sources identified and biological risk assessed, remedial resources can be efficiently allocated.

Historically, industrial discharge, chemical spills, improper waste disposal and urban runoff have been the largest known toxin sources. These sources are easily identifiable so that toxin discharge is controllable. Now, a significant portion of aquatic contamination is believed to come via pore water and particulate bound contaminate exchange in benthic sediment (i.e. soluble toxins are suspended and leached from underwater sediment into the aquatic environment).

Sedimentary (benthic) contamination is particularly troublesome to remedy because, unlike contamination caused by chemical spills and industrial discharge, the toxin source is often difficult to identify. Benthic contamination also creates a high level of biological risk for benthic organisms whose survival depends directly on the condition of the underwater sediment. Additionally, all aquatic organisms are put at risk of contamination as toxins in the underwater sediment migrate across the sediment-water interface and contaminate the aquatic environment. Due to the scope and seriousness of problems associated with benthic contamination, ways of assessing the biological risk associated with toxins in benthic sediments have been developed.

The biological risk is dependent, not only on toxin concentrations, but on the rate at which marine plants and animals uptake and accumulate harmful toxins. This rate must be determined. Direct measurement, however, of uptake and accumulation is extraordinarily difficult. Fortunately, indirect measurement is possible. This is accomplished by measuring the rate at which soluble toxins become suspended, leach through pore water, cross the sediment water boundary and enter the aquatic environment. This is called the benthic flux rate.

The benthic flux rate is the most accurate known indicator of the rate at which toxins are entering an aquatic environment and of associated biological risk. The benthic flux rate also is useful in pin pointing the source of contamination by determining whether toxins are leaching from the sediments into the water or vice versa. Together with traditional monitoring and assessment techniques, benthic flux measurements are useful in remedying contamination of benthic sediments.

At present, the best known approach for measuring the benthic flux rate requires isolating a volume of water against a water body floor and periodically sampling the isolated water. In this way, toxin concentration measurements are periodically made and changes in these concentrations are detected. Importantly, because changes in toxin concentrations are generally very small, other factors which could affect toxin concentration measurements and mislead researchers must be eliminated.

Many biological and geochemical processes are affected by dissolved oxygen contained in water samples. Oxygen conditions must, therefore, be maintained during sampling to obtain results which are accurately reflective of the natural environment. More specifically, respiration and oxidation processes tend to deplete oxygen. In the ocean, this depleted oxygen is normally replaced by oxygen introduced through the water-air interface through wave action and through various biological processes such as photosyntheses. In an isolated sample, however, depleted oxygen is not adequately replaced. As a result, oxygen dependent reactions which affect toxin levels fail to continue in a normal manner and make benthic toxicant flux rate measurements inaccurate.

In view of the inaccuracy caused by oxygen depletion while isolating fluid during sampling, a need has been recognized in accordance with this inventive concept for an improved method and apparatus for introducing oxygen into a closed benthic flux sampling chamber and maintaining appropriate oxygen levels to insure the integrity of the benthic flux sampling process and to allow precise and accurate benthic flux rate determinations.

SUMMARY OF THE INVENTION

In accordance with the present invention, a method and apparatus for maintaining oxygen concentrations in an isolated fluid sample are provided (e.g. in a sample chamber of a benthic flux sampling device). Generally, the apparatus includes a sensor system for measurement of the oxygen concentration in the sample, an oxygenation system for introducing oxygen into the fluid sample (e.g. ocean water) and a control unit for monitoring data gathered from the sensor system and controlling the oxygenation system.

The sensor system of the present invention includes an oxygen sensor attached to a sample container which is connected electronically through an oxygen sensor cable to the control unit. The oxygen sensor, more specifically, is a flow-through type and the sensor system includes a pump for pumping fluid from the container and past the oxygen sensor to measure oxygen concentrations in the fluid. The control unit continuously monitors the oxygen sensor and thus, oxygen concentrations in the sample.

The oxygenation system includes an oxygen storage tank, a pressure regulator, an oxygen control valve, and an oxygen dispenser. The pressure regulator is attached to the oxygen storage tank and is capable of adjustment to regulate oxygenation system pressure and control the rate at which oxygen is dispensed into the sample. A first stage diving pressure regulator is used in the preferred embodiment of the invention and maintains a desired constant pressure within the oxygen dispenser to dispense oxygen at a desired constant rate.

The oxygen control valve is a twelve volt latching solenoid valve connected with the control unit through an oxygen control valve cable for selective activation and deactivation of the oxygenation system. During activation, the oxygen control valve opens in response to a signal generated by the control system when oxygen concentrations fall below minimum allowable levels. Activation pressurizes the oxygenation system and begins oxygen delivery. During deactivation, on the other hand, the oxygen control valve closes in response to another signal generated from the control system when oxygen concentrations rise above maximum allowable levels to de-pressurize the oxygenation system and stop oxygen delivery.

The oxygen dispenser is capable of efficiently dispensing oxygen into a fluid sample at underwater pressures. For the purposes of the instant invention, an oxygen diffuser is employed. The oxygen diffuser specifically includes an oxygen permeable, thin-walled teflon tube approximately fifty meters long and having a four millimeter outside diameter. The tube is coiled in the container and is capable of dispensing oxygen into water at a rate dependent on oxygen pressure. Ideally, the diffuser is capable of dispensing oxygen when pressurized to near two hundred p.s.i.

The method of maintaining a constant oxygen concentration in a fluid sample includes establishing a desired (e.g. ambient) oxygen concentration by measuring and averaging oxygen concentrations found at the deployment site. With the ambient oxygen concentration established, maximum and minimum allowable oxygen concentration values are established based on a predetermined range of variability. Sample oxygen concentrations are measured periodically by the oxygen sensor system and the oxygen sensor system is continually monitored by the control unit. When oxygen concentrations fall below the minimum allowable value, the oxygenation system activates and pressurizes to deliver oxygen to the sample. When oxygen concentrations rise above the maximum allowable value, the system depressurizes and oxygen delivery ceases. Thus, oxygen concentration levels are maintained in the sample.

Accordingly, it is an object of the present invention to provide a method and apparatus for delivering oxygen to oxygenate a fluid sample.

It is another object of the present invention to provide a method and apparatus capable of automatically maintaining constant oxygen concentrations in a fluid sample without operational oversight.

It is yet another object of the present invention to improve the integrity of benthic flux sampling.

Another object of the invention is to deliver oxygen to a fluid sample to maintain the ambient concentration of oxygen within a specified range.

Another object of the invention is to deliver oxygen without contaminating the samples.

These and other objects of the invention will become more readily apparent from the ensuing specification and claims when taken in conjunction with the appended drawings.

BRIEF DESCRIPTION OF THE DRAWINGS

FIG. 9b is a flow chart depicting logical steps utilized by the oxygenation system depicted in FIG. 9a.

FIGS. 10a, 10b, and 10c, are illustrations of deployment of the benthic flux sampling device and FIGS. 10d, 10e, 10f and 10g are illustrations of retrieval of the device.

DESCRIPTION OF THE PREFERRED EMBODIMENT

Figure 1:
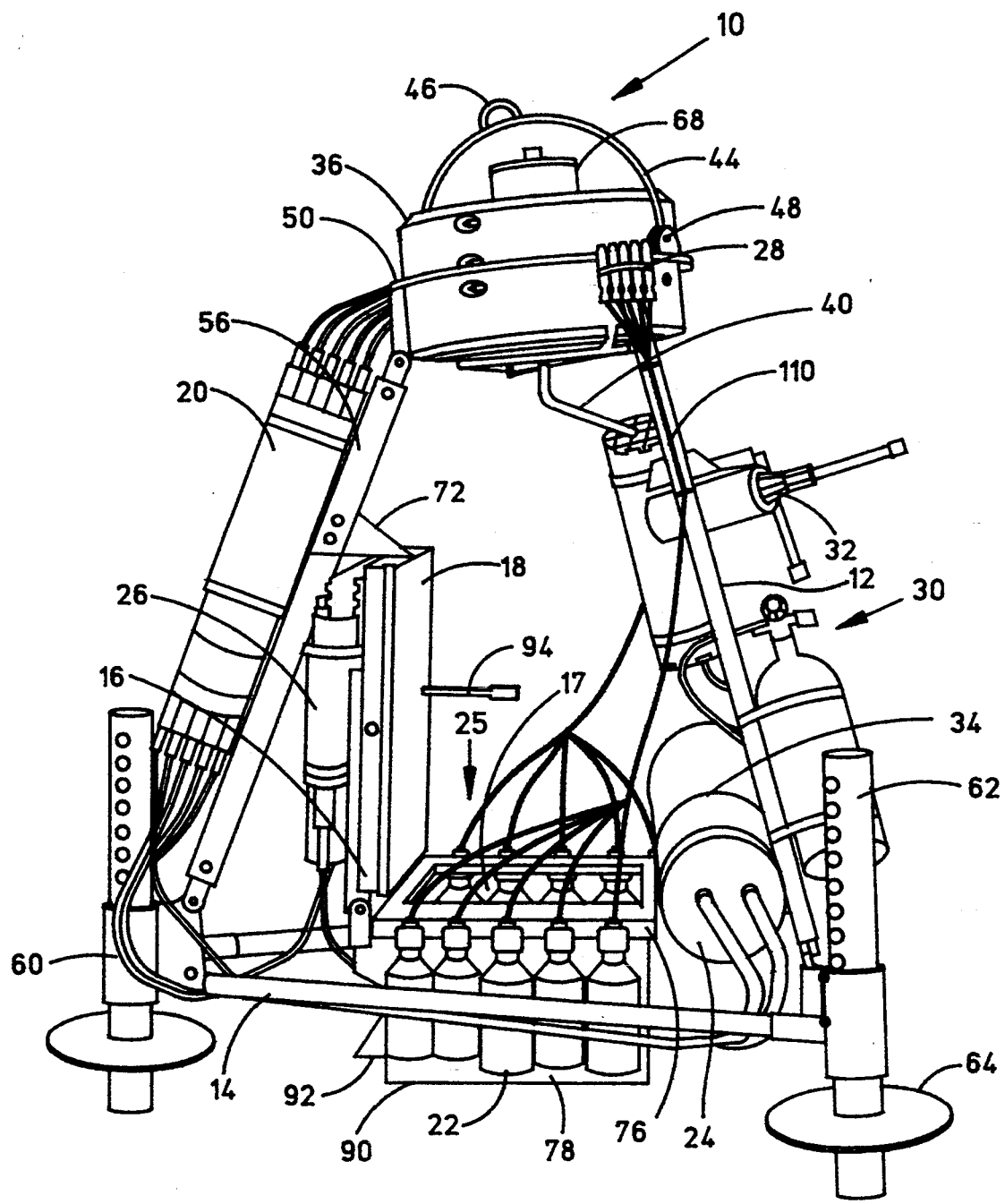
FIG. 1 is an isometric view of the benthic flux sampling device.

Referring to FIG. 1 of the drawings, a benthic flux sampling device 10 is shown that is capable of periodically sampling water to determine the movement of various selected toxins across a fluid boundary (e.g. ocean floor). Benthic flux sampling device 10 includes a tripod shaped frame 12 having a triangular base 14 to provided stability and to support device 10 during deployment on a variety of terrain types. A box shaped container 16 which defines a sample chamber 17 is attached to base 14 and serves to isolate a volume of water during operation.

Several systems are included with the benthic flux sampling device to facilitate benthic flux sampling and data gathering. A fluid sampling system 25 is provided to sample water isolated within chamber 17 and store a plurality of samples. A sensor system 26 monitors variables such as temperature, salinity, pH, dissolved oxygen content and fluid flow of water within chamber 17. An oxygenation system 30 maintains ambient oxygen concentration levels within chamber 17. Sensor system 26, sampling system 25 and oxygenation system 30 are monitored by and may be controlled by control unit 20. Variables sensed by the sensor system effect various detectable toxin levels and are closely monitored and recorded by control unit 20 to assure integrity of the sampling process.

Figure 2:
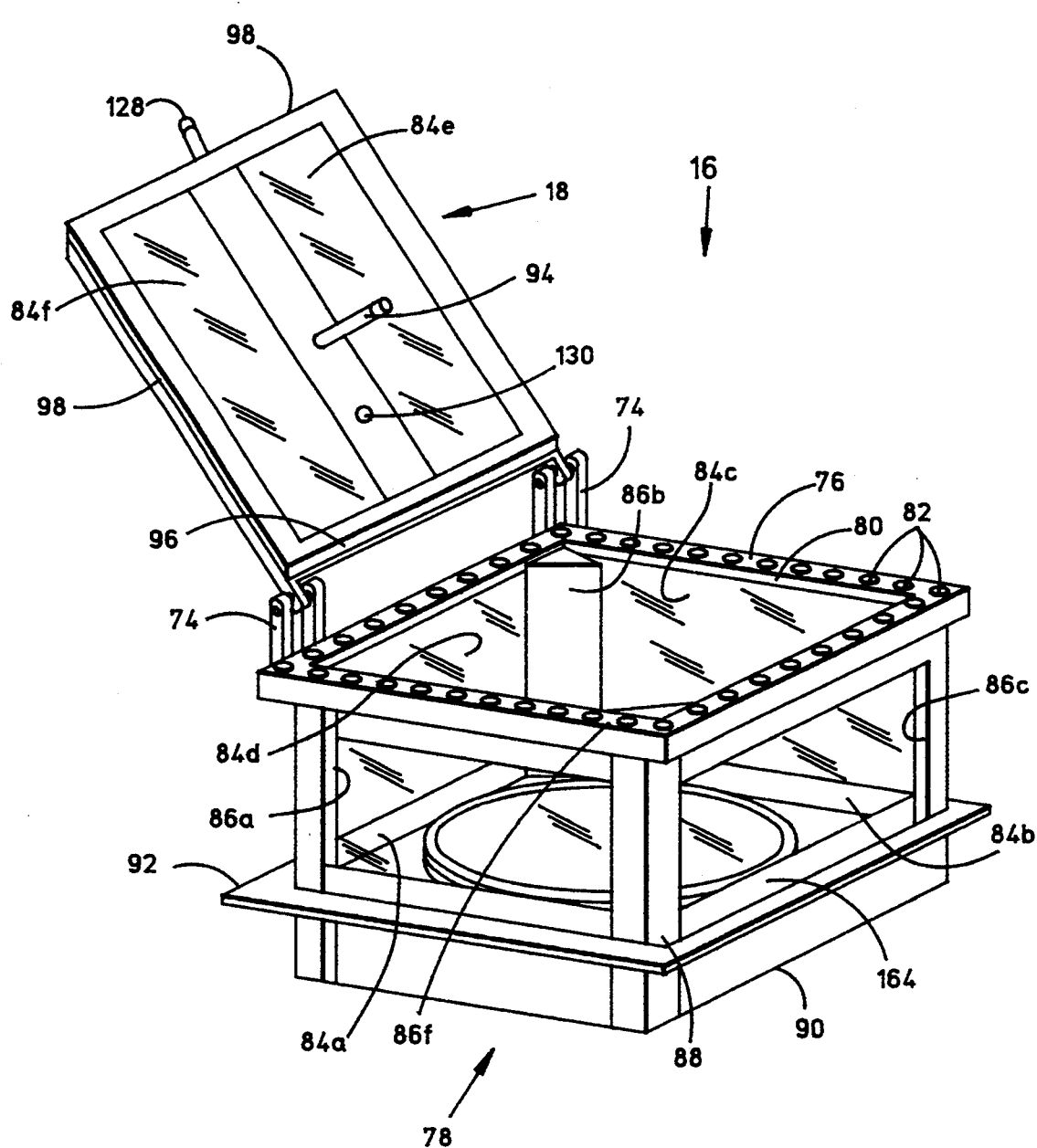
FIG. 2 is an isometric view of the container which encloses the sampling chamber of the benthic flux sampling device.
Figure 3:
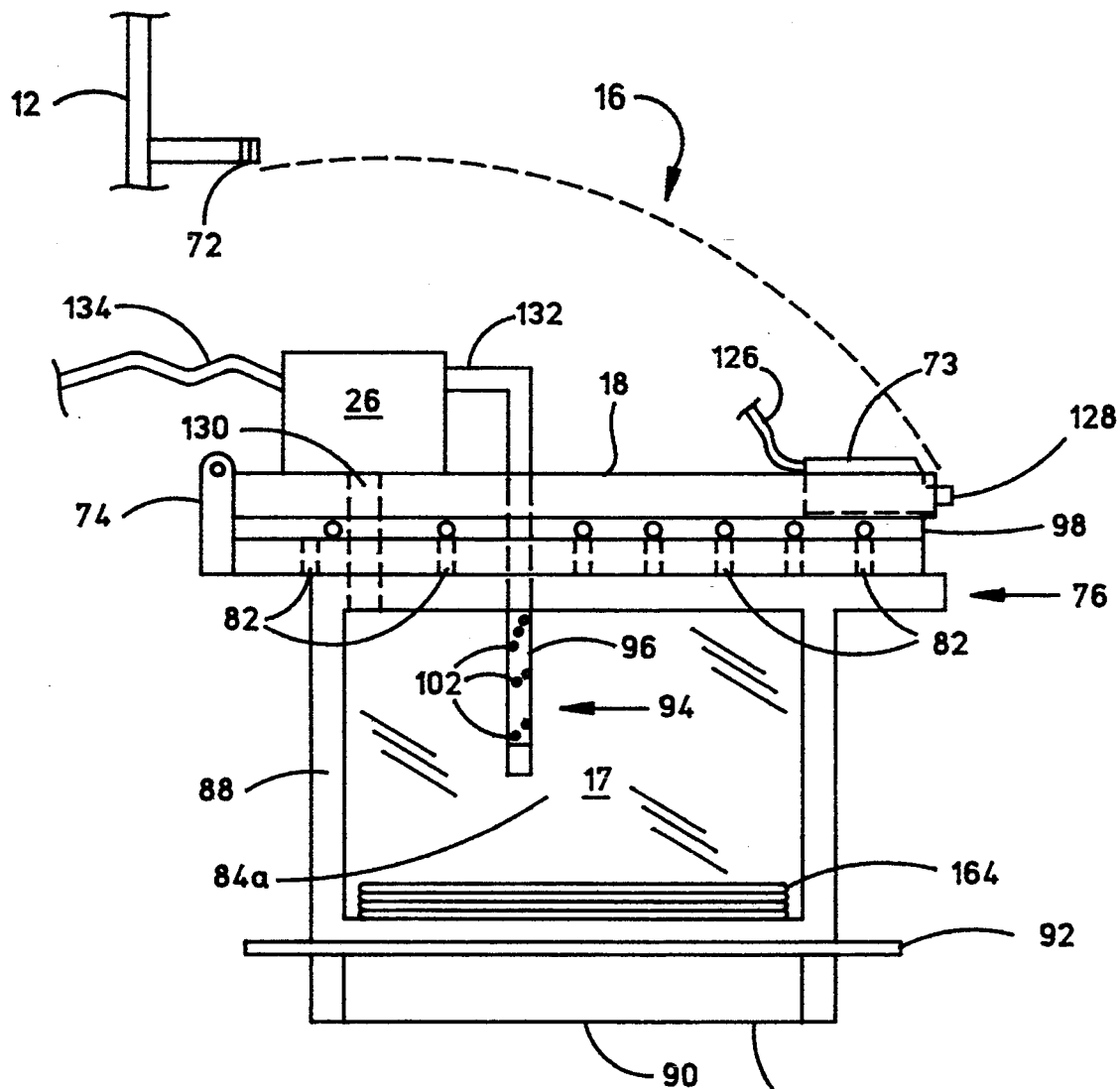
FIG. 3 is a side view of the container depicted in FIG. 2.

The preferred embodiment of container 16 of benthic flux sampling device 10 is shown in FIG. 2 and FIG. 3 and includes an open top surface 76 with a lid 18, an open bottom 78 and four translucent or transparent panels 84a–84d.

Lid 18 having a steel bar 98 bolted to its perimeter is attached to the top surface 76 of container 16 by a pair of hinges 74 which securely interconnect lid 18 with top surface 76. Lid 18 is rotatable about hinges 74 from an open position as shown in FIG. 2 to a closed position as shown in FIG. 3 for purposes which will be elaborated on below. Lid 18 is formed with translucent panels 84e and 84f to allow ambient light to penetrate to the interior of container 16.

A multitude of bar magnets 82 are held within the perimeter of top surface 76 to hold lid 18 securely when lid 18 is closed against top surface 76. Lid 18 is slightly smaller in area than top surface 76 to align steel bar 98 with magnets 82 and to magnetically secure lid 18 in the closed position. To inhibit corrosion, a clear layer of plastic coats top surface 76 and magnets 82. A deformable tubular gasket 80 is held within the perimeter of top surface 76 inside of magnets 82 to optimize the seal between lid 18 and top surface 76. Gasket 80 may be made of silicone or any other suitable material capable of forming a water tight seal.

A lid release 73 is securely mounted to the exterior of lid 18 on a side opposing lid hinges 74 (see FIG. 3). Lid release 73 includes a reciprocally moveable release bar 128 which normally protrudes beyond the periphery of lid 18 to engage a recessed portion of lid release hook 72 to hold lid 18 in an open position as shown in FIG. 1. Control line 126 electronically connects lid release 73 to control unit 20 (see FIG. 3). Accordingly, in response to an electronic signal from control unit 20, release bar 128 will be withdrawn and lid 18 will fall due the force of gravity into a closed position as shown in FIG. 3.

Although lid 18 is described as a magnetically sealable hinged lid, any of a number of suitable lid types, gaskets and control mechanisms may be effectively utilized in accordance with the inventive concepts disclosed herein. One skilled in the art to which this invention pertains could therefore select other suitable lids which are able to automatically close and seal after deployment.

Bottom 78 of container 16 is provided with an edge. The edge, more specifically is a metallic knife edge periphery 90 which pierces the ocean floor during deployment, embeds bottom 78 within the ocean floor and seals container 16 against the ocean floor. A peripheral skirt 92 extends horizontally outwardly from container bottom 78. Skirt 92 is more specifically positioned inches above the knife edge periphery 90 of container bottom 78 and seals against the ocean floor surface and to support container 16 during deployment.

Container 16 includes a rigid support frame 88 and supports transparent panels 84a–84d to resist deep water pressures. Prism shaped blocks 86a–86d of transparent material are disposed in the corners of container 16 to inhibit stagnation of water in chamber 17. In the right angles formed between top surface 76 and lid 18 /r between bottom 78 and the water body floor, additional blocks may be attached if desired. Blocks 86 and panels 84 are fabricated from clear poly-carbonate or other high strength and non-corrosive translucent material to allow light to pass, resist corrosion and resist deep water pressures.

It can be appreciated that although container 16 is box shaped and blocks 86 are referred to as prism shaped to appropriately fit into container 16, a suitable alternative configuration could be selected in accordance with this inventive concept by one skilled in the art to which this invention pertains. For example, an embodiment of benthic flux sampling device 10 may be utilized having a container which is not box shaped and where blocks 86 are eliminated or adapted in shape and position to similarly prevent stagnation of fluid in the container and achieve the goal of benthic flux sampling.

Figure 4A:
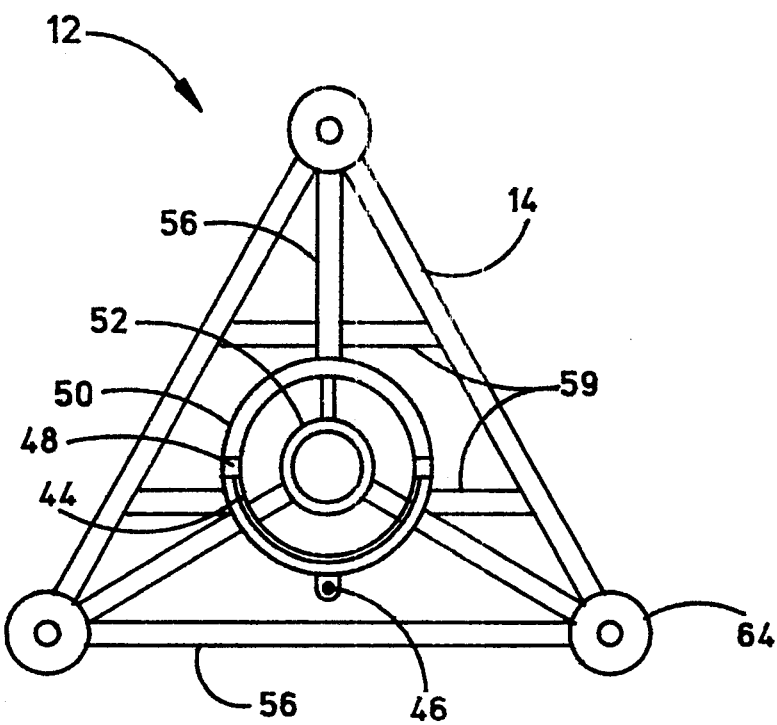
FIG. 4a and FIG. 4b are top and side views respectively of the frame of the benthic flux sampling device.
Figure 4B:
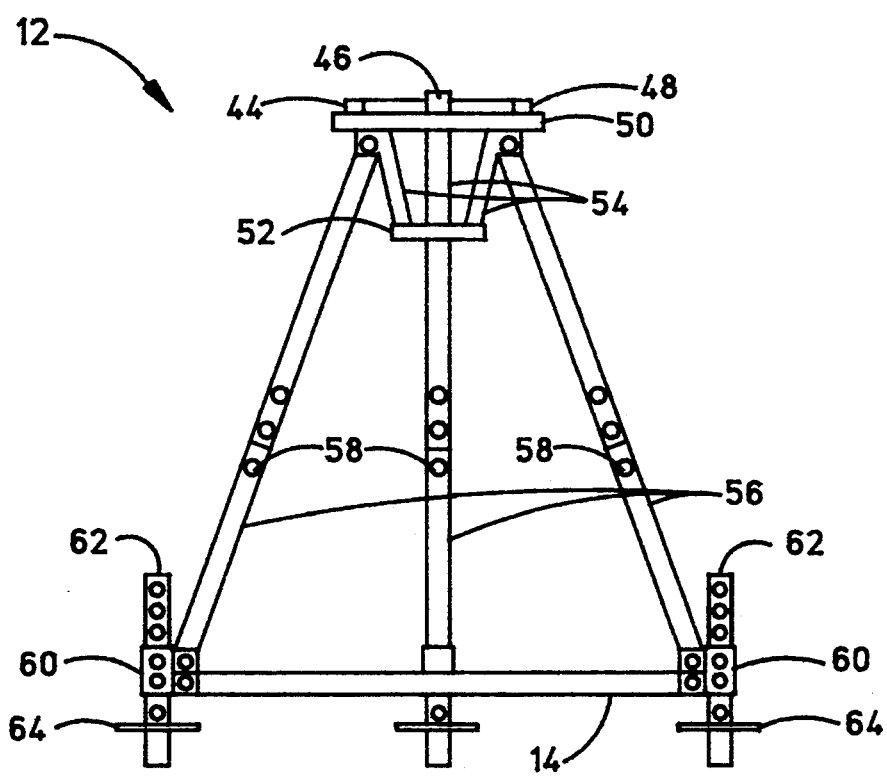

Frame 12, noting in FIG. 4a and FIG. 4b is fabricated from a corrosion resistant material such as stainless steel or coated with an appropriate non-corrosive coating such as paint to inhibit corrosion. The weight of frame 12 combined the weight of container 16 is sufficient so that the benthic flux sampling device is non-buoyant in sea water to facilitate deployment.

Frame 12 is provided with a tubular support ring 50. Ring 50 supports a lifting bail 44 having a padeye 46 to serve as a convenient grip during deployment and retrieval. Lifting bail 44 is a rigid arc shaped member having each of its two ends mounted on a respective bail hinge 48. Bail hinges 48 are, in turn, mounted on diametrically opposing points on buoy support ring 50. FIG. 1 depicts lifting bail 44 in an operational position where bail 44 extends vertically upright to allow device 10 to be hoisted upwards. FIG. 4b, alternatively, depicts lifting bail 44 in a resting position that normally lies horizontally upon support ring 50 and does not interfere with the release of retrieval buoy 36. Buoy support ring base 52 is held by three rigidly attached buoy support arms under support ring 50 for holding buoy 36 during operation. As shown in FIG. 4b, three equal length frame arms 56 are bolted to support ring 50. The frame arms extend from support ring 50, past ring base 52 to each corner of triangular base 14 to provide a rugged structure. Frame arms 56 are securely bolted to each of three mounts 60. Each of the frame arms 56 are provided with a sliding frame arm adjustment 58 located near the midpoint of each to allow for a slidable adjustment so that frame is adaptable for use with various types of sensors and systems. In FIG. 4a, a pair of parallel cross bars 59 are shown attached to and extending between adjacent sides of triangular base 14 for additional rigidity and to support container 16.

Referring again to FIG. 4b, each of three adjustable legs 62 extend through each mount 60 for absorbing impact when the benthic flux sampling device is deployed on the ocean floor. Each leg 62 is formed with a plurality of juxtaposed holes for selective vertical alignment with at least one hole provided in each mount 60. With each leg 62 adjusted as desired, a bolt is inserted through the aligned holes to hold leg 62 in mount 60. A flat disk shaped foot 64 is attached to leg 62 at a desired position. It can be appreciated that adjustment of each leg 62 can be used to optimize the seal between container 16 and the ocean floor during deployment.

Although the preferred embodiment of frame 12 is disclosed as above, any one of a number of frame configurations could be utilized in accordance with the present inventive concept. One skilled in the art to which this invention pertains, for example, could select any number of suitable frames to effectively accomplish the task of benthic flux sampling as substitute to the preferred embodiment disclosed above.

Referring once again to FIG. 1, a video camera 32 is attached to frame 12 on a frame arm 56 in a manner suitable to film the sealing arrangement made between container 16 and the sedimentary floor during deployment. Camera 32 may also be used during deployment of benthic flux sampling device 10 to facilitate selection of a desirable landing site. It can also be appreciated that camera 32 is useful for monitoring the sampling process and is capable of transmitting images to a remote monitor. Video camera 32 is also capable of receiving remotely transmitted instructions so that the position of camera 32 may be selected as desired and camera 32 may be selectively turned on and off.

Benthic flux sampling device 10 as shown in FIG. 1 is further provided with a two piece syntactic foam float retrieval buoy 36 that floats free from frame 12 to the water body surface in response to an acoustic signal to facilitate retrieval of benthic flux sampling device 10. A retrieval line 40 is attached between frame 12 and retrieval buoy 36 and is normally coiled in a retrieval canister 42 which is attached to frame 12 under buoy 36. After retrieval buoy 36 releases from frame 12, buoy 36 floats to the water surface, drawing retrieval line 40 from retrieval line canister 42. Buoy 36 and retrieval line 40 are retrieved at the water surface by an operator and retrieval line 40 is used to hoist the benthic flux sampling device to the water surface as shown in FIG. 10e and FIG. 10f.

Figure 5A:
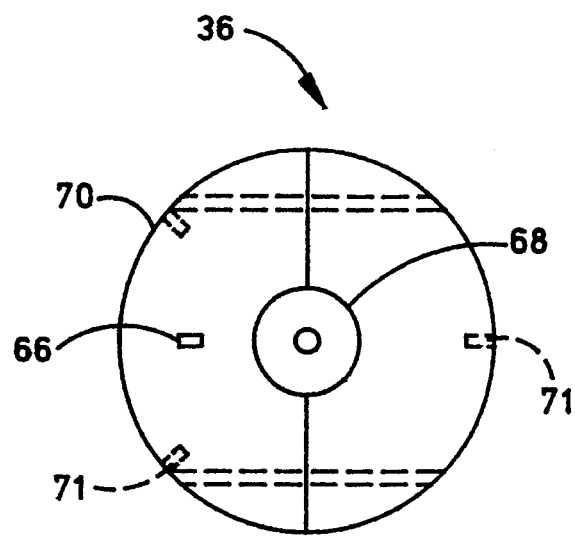
FIG. 5a and FIG. 5b are top and side views respectively of the retrieval buoy.
Figure 5B:
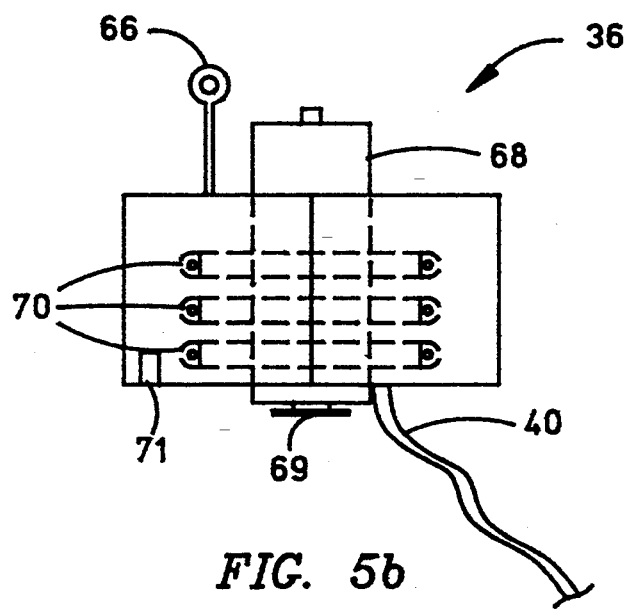

As shown in FIGS. 5a and 5b, retrieval buoy 36 is approximately cylindrically shaped for fitting into frame 12 within buoy support ring 50 until released. Buoy 36 is also equipped with a retrieval hook 66 to aid in retrieval. It can be appreciated by those skilled in the art that buoy 36 may be of any shape suitable to be held on frame 12 and released to the water surface to facilitate retrieval of benthic flux sampling device 10.

A remotely actuated acoustic release 68 is coaxially disposed within buoy 36. The release is actuated remotely to rotate a hook 69 which is attached to the bottom portion of acoustic release 68. Hook 69 is normally latched to frame 12 on a portion of buoy support ring base during deployment, but hook 69 unlatches from frame 12 in response to rotation caused by acoustic release 68. When released, buoyant forces lift buoy 36 from buoy support ring 50 to the water surface. Acoustic release 68 is an appropriate release such as that marketed by Endeco Corporation under the designation Endeco Type 900 Acoustic Release which is preprogrammable for actuation in response to a remotely initiated coded signal for increased security and to prevent vandalism.

Although the preferred embodiment of the acoustically releasable retrieval buoy is disclosed as above, any one of a number of suitable sampling system configurations could be utilized in accordance with the present inventive concept. One skilled in the art to which this invention pertains could select any number of suitable retrieval mechanisms to effectively accomplish the task of retrieving device 10 as a substitute to the preferred embodiment disclosed above.

Figure 6:
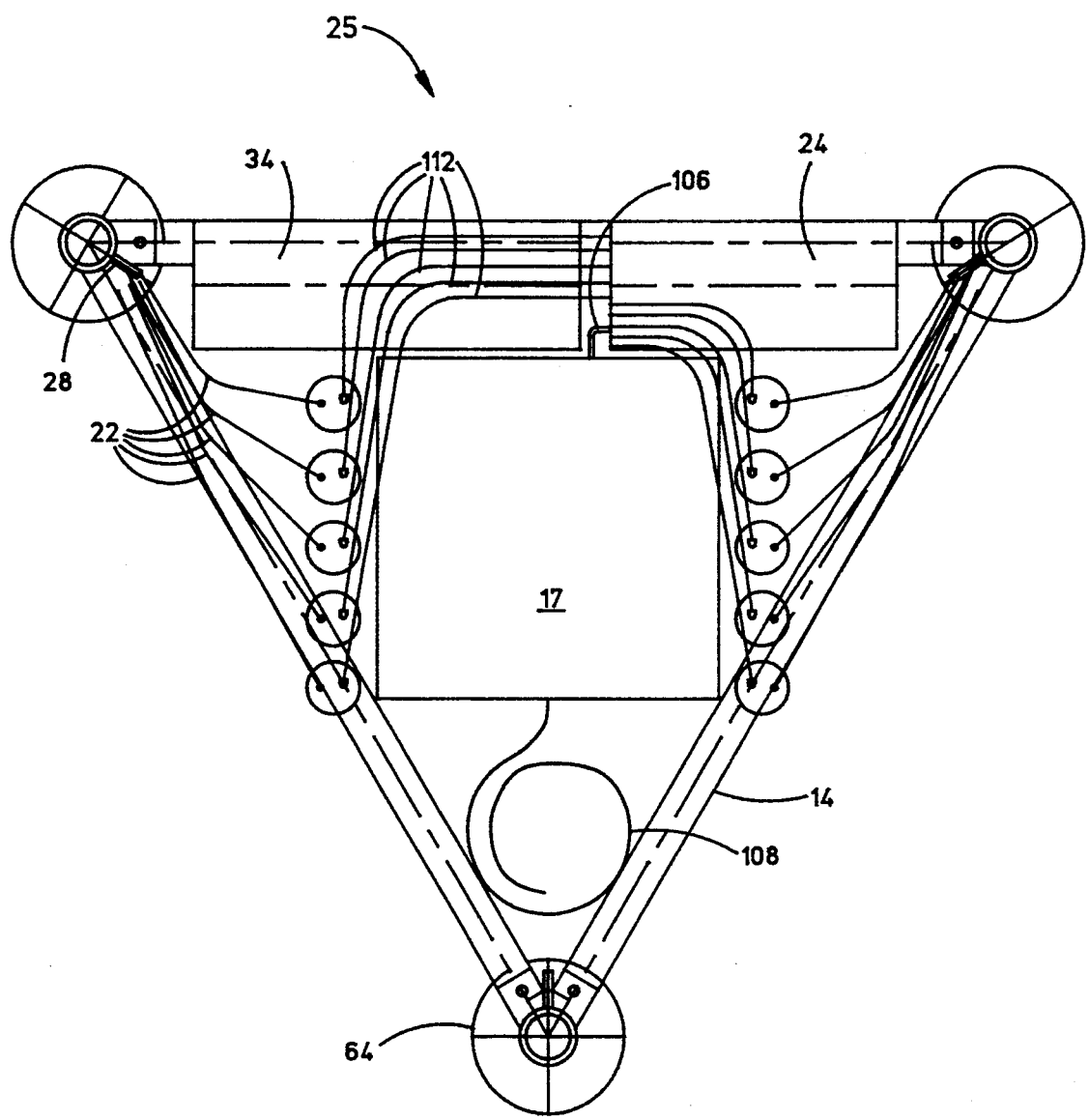
FIG. 6 is a modified top view illustrating the layout of the sampling system of the benthic flux sampling device.
Figure 7:
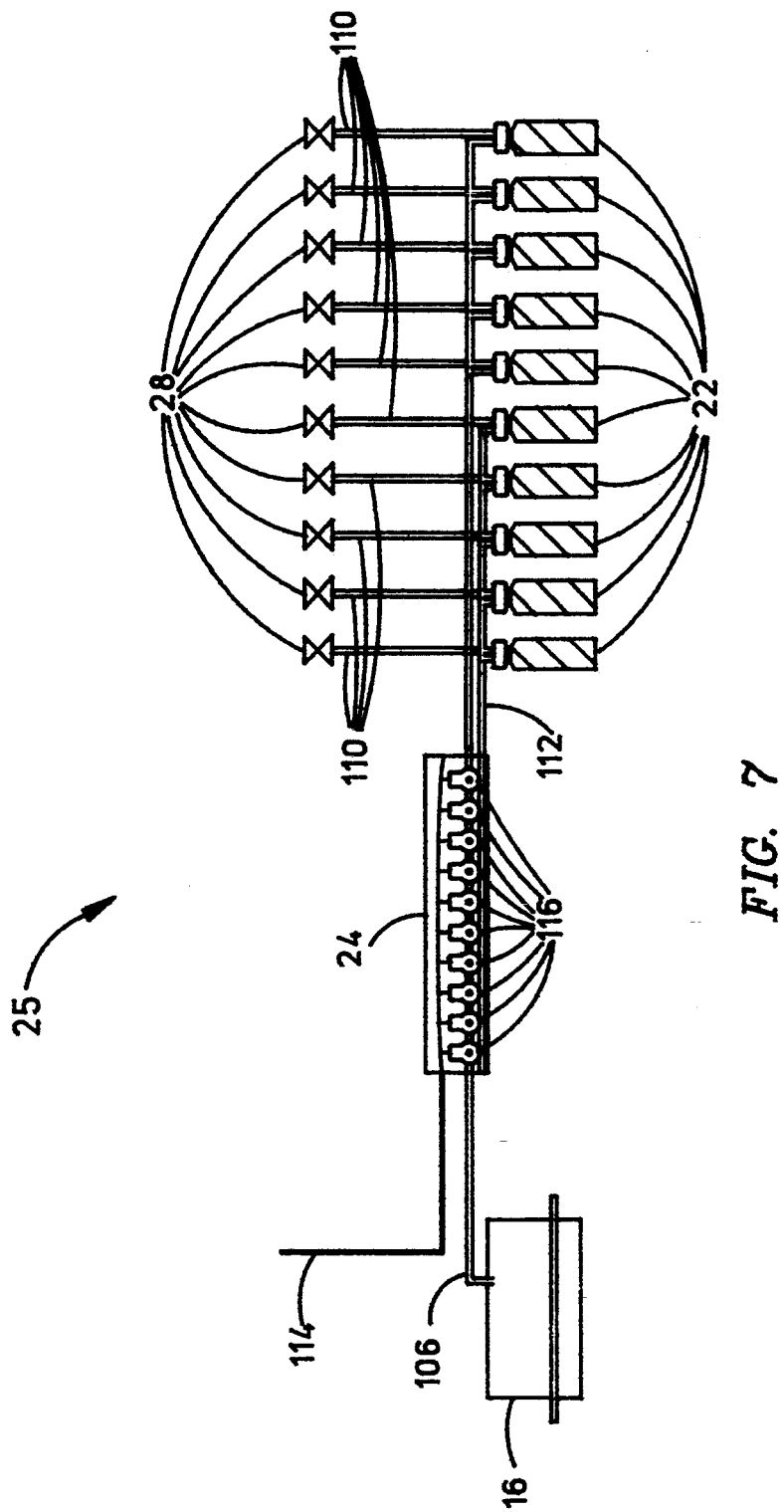
FIG. 7 is a schematic diagram of the sampling system of the benthic flux sampling device.

Looking to FIG. 6 and FIG. 7, fluid sampling system 25 is shown and includes appropriately connected supply line 106, valve manifold 24, sample lines 112, sample bottles 22, vent lines 110 and check valves 28. In the preferred embodiment of the benthic flux sampling device, sampling system 25 includes ten sample bottles 22 for periodically storing 10 separate samples from the volume of water contained in the container 16 to validate benthic flux determinations. Bottles 22 are attached, for easy removal, to base 14 in a position adjacent container 16. Each sample bottle 22 is connected in fluid communication with a corresponding valve 116 by a sampling line 112 to regulate sampling.

Valves 116 are held in a water-tight valve manifold 24 to allow valves 116 to be unaffected by deep ocean conditions during operation. Valves 116 are, in turn, connected in fluid communication with chamber 17 of container 16 through supply line 106. Valves 116 are appropriate valves such as marketed by Galtek Incorporated under the designation Galtek 203-1414-115 ¼ inch solenoid valves. Each valve is independently electronically controlled by control unit 20 through a corresponding valve control line 114.

Sample bottles 22 may be a standard design in any appropriate volume, material or shape so that bottles are easily connected and removed from with sample line 112 and vent line 110. It is intended, however, that the total volume of samples taken from chamber 17 not exceed 10% of the volume of container 16 to assure reliability of the sampling process. Bottles 22 must be strong enough to withstand underwater pressure and maintain a water tight seal. Sample bottles 22 are preferably fabricated from teflon to minimize contamination of samples and to facilitate cleaning. It can be further appreciated that sample bottles 22 may be pre-loaded with preservatives such as acid so that samples will be immediately stabilized at the moment of collection.

Check valves 28 are attached on the upper portion of frame arms 56 as depicted in FIG. 1. Check valves 28 are each connected in fluid communication with a separate sample bottle 22 through a corresponding vent line 110.

Replenishment line 108 is seen in FIG. 6 connected in fluid communication with container 12 and extends outwardly from container 12 to adjacent the exterior of container 12. Thus, a discrete volume of water equal to the volume of water sampled is drawn from adjacent container 12 through replenishment line 108 to instantaneously replace the volume of water taken for sampling. Sample lines 112, supply line 106, vent lines 110 and replenishment line 108 are preferably fabricated from teflon to minimize the potential for contamination of samples. Each line is attachable by means well known in the art to facilitate removal for cleaning.

Although the preferred embodiment of sampling system 25 is disclosed as above, any one of a number of suitable sampling system configurations could be utilized in accordance with the present inventive concept. One skilled in the art to which this invention pertains could select any number of suitable sampling systems to effectively accomplish the task of drawing and storing samples from a sampling chamber as a substitute to the preferred embodiment disclosed above.

Figure 8:
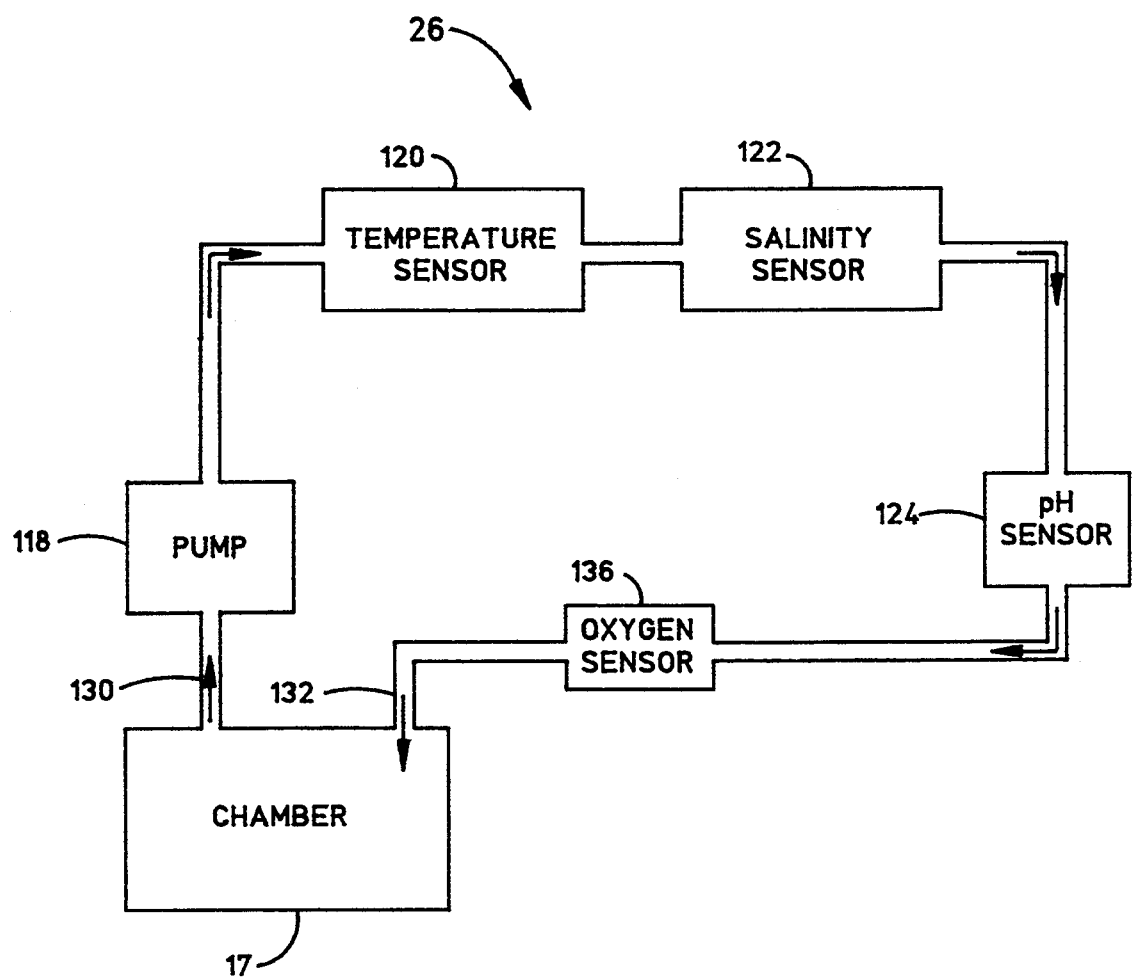
FIG. 8 is a block diagram of the sensor system of the benthic flux sampling device.

In FIG. 8, a block diagram of sensor system 26 is shown. System 26 is mounted on lid 18 and includes sensor system inlet 130 which is an opening in lid 18 to chamber 17 and a sensor system outlet 132 which is also an opening in lid 18 (see FIG. 3). Pump 118, temperature sensor 120, salinity sensor 122, pH sensor 124 and oxygen sensor 136 are mounted on lid 18 in series between inlet 130 and outlet 132 so that a fluid circuit is established to measure the required characteristics of the sample. Pump 118 maintains water circulation through the sensor system. Typically, the pump can be a commercially available submersible pump having a flow rate of approximately 90 milliliters/second.

Temperature sensor 120 should be an aged thermistor that is pressure protected, shock and vibration resistant. Preferably an appropriate temperature sensor such as marketed by Sea Bird Electronics Corporation under the designation Model SBE 3 is used. Salinity sensor 122 is 2-terminal, 3-electrode (platinum) flow-through type conductivity sensing element. An appropriate salinity sensor capable of use in determining salinity of ocean water may be one such as is marketed by Sea Bird Electronics Corporation under the designation Model SBE 4 Conductivity Meter. The pH sensor 124 measures the pH with a combination type probe using a pressure balanced teflon junction Ag/Ag—Cl reference electrode. Preferably, the pH sensor is an appropriate sensor such as marketed by Sea Bird Electronics corporation under the designation Model SBE 18 pH sensor. Sensors, 120, 122, 124, and pump 118 are each appropriately coupled in electronic communication with control unit 20 through a sensor cable 134.

Oxygen sensor 130 is preferably a "Beckman" polarographic type which produces an oxygen dependent electrical current such as that marketed by Seabird Electronics corporation under the designation Model SBE 13. Oxygen sensor 136 is connected through oxygen sensor cable 162 to control unit 20.

Control unit 20 is preferably a Seabird Electronics model SBE 19 Seacat Profiler modified to facilitate control of the operation of device 10, although any one of several suitable units could have been selected. Control unit 20 periodically collects and records data such as the flow rate of pump 118, and data from sensor system 26. Control unit 20 is able to control lid closure, fluid flow by selective activation of pump 118, sensor system 26, sampling system 25 and oxygenation system 30. Control unit 20 also regulates and monitors valves 116. All sensors, valves, control unit 20 and pump 118 may be suitably connected to battery case 34 to fulfill electric power be requirements and so device 10 can function autonomously.

Figure 9A:
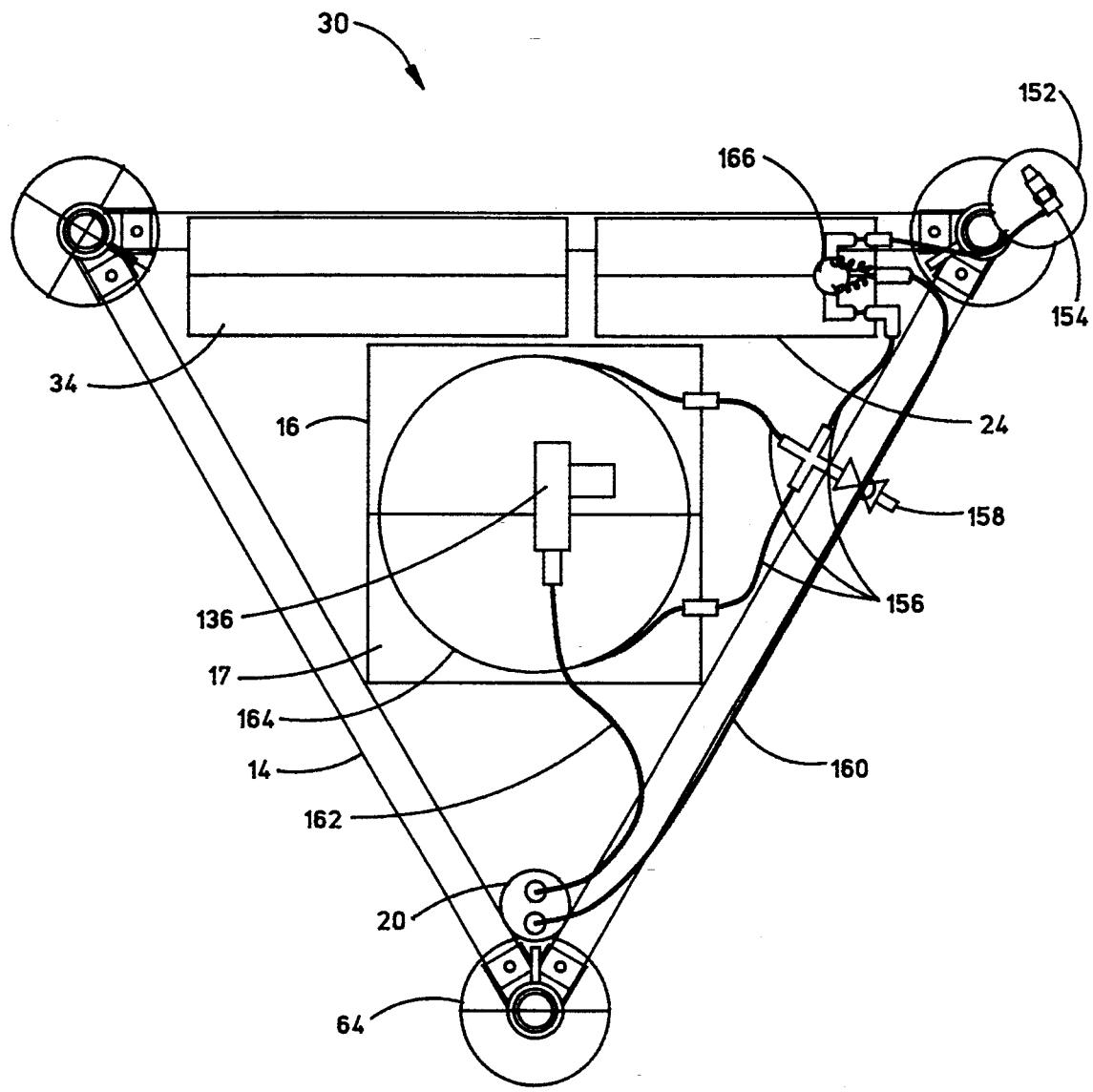
FIG. 9a is a modified top view illustrating the oxygenation system of the benthic flux sampling device.

Looking now at FIG. 9a, oxygenation system 30 includes an oxygen supply tank 152 connected with an oxygen pressure regulator 154, a supply line 156, a bleed valve 158, an oxygen control valve 166, and an oxygen dispenser 168 for maintaining ambient oxygen levels in the sample of water isolated in chamber 17 of container 16. With ambient oxygen concentrations maintained, the integrity of the sampling process is improved to validate a benthic flux determination.

Oxygen supply tank 152 is a 13 cubic foot aluminum diving tank equipped with a first stage pressure regulator 154 for providing a suitable output pressure to the oxygenation system. Pressure regulator 154 is adjustable for selective pressure adjustment within the oxygenation system to facilitate oxygenation of a sample at various underwater pressures. Although the preferred embodiment utilizes an adjustable pressure regulator, there are numerous other suitable configurations. For example, those skilled in the art to which this invention pertains could utilize a pressure regulator which is automatically adjustable to automatically regulate pressure within oxygenation system 30 during operation at various depths.

Oxygen supply line 156 is a teflon tube with appropriate fittings for attachment between pressure regulator 154 and the oxygen dispenser 168. Oxygen supply line 156 extends in fluid communication from pressure regulator 154 to oxygen control valve 166 then to bleed valve 158, where, oxygen supply line 156 splits, extends through container 16 in two places and attaches to each of two ends of oxygen diffuser 164 in container 16 to deliver oxygen from oxygen storage tank 152 (see FIG. 9a). Bleed valve 158 is connected to supply line 156 to facilitate flushing of and to prevent over pressurization of oxygenation system 30.

Figure 9B:
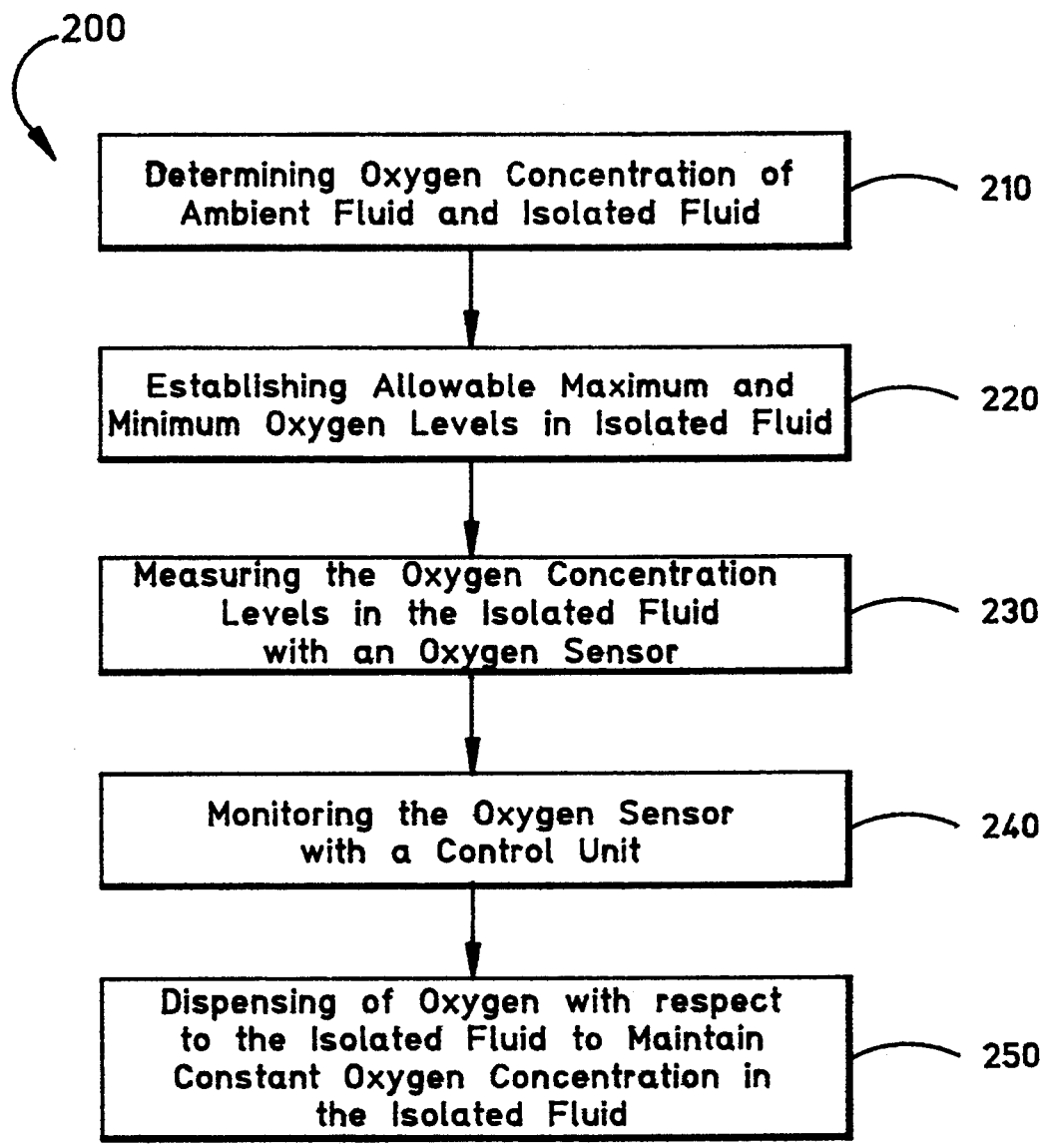

Control unit 20 is connected to oxygen control valve 166 by oxygen control valve cable 160 to communicate electronic signals initiated by control unit 20 to selectively open or close oxygen control valve 166 (see FIG. 9b). Control valve 166 is a 12 volt, latching solenoid valve housed within valve manifold 24 to selectively regulate the flow of oxygen through supply line 156 of oxygenation system 30. Oxygen sensor cable 162, a component of sensor cable 134, connects control unit 20 with oxygen sensor 136 electronically so that data collected by oxygen sensor 136 may be continuously monitored by control unit 20.

Oxygen dispenser 168 is capable of dispensing oxygen at various depths. According to the preferred embodiment, oxygen diffuser 164 is used. Oxygen diffuser 164, more particularly, is a coil of thin-walled, four-millimeter outer diameter teflon tube which is permeable to oxygen gas and has an overall length of fifty meters. The diffuser 164 has a uniform diameter and, as shown in FIG. 2 and FIG. 3, the diffuser is coiled and mounted in container 16 to dispense oxygen into a water sample at a rate depending on the oxygen pressure. Thus, when oxygen is regulated at a selected constant pressure (e.g. 1500 p.s.i.), oxygen is dispensed at a constant rate. It can also be appreciated that although a uniform diameter, teflon tube is disclosed as the preferred embodiment of oxygen dispenser 168, a number of other suitable configurations and materials may be selected. That is having the teachings herein disclosed those skilled in the art to which this invention pertains could choose other configurations and materials which could adequately dispense oxygen into water.

Operation

Benthic flux sampling device 10 must be prepared prior to deployment to insure the integrity of the samples to be taken with the device. The entire system including the sensor system, all plumbing lines, and sample bottles must be cleaned with solutions appropriate for the analyses to be performed on the collected samples. Batteries must be charged, and a check of the acoustic release and oxygen systems must be performed to insure successful deployment, sampling and retrieval.

Once benthic flux sampling device 10 is prepared and all systems are operating properly, the device can be lowered into the water following a general procedure as seen in FIGS. 10a through 10c. To lower device 10, deployment cable 168 is connected to the padeye 46 of lifting bail 44. Device 10 is deployed or placed having lid 18 open as shown in FIG. 1 to minimize disturbance of sediment during initial contact with a water body floor and to facilitate ambient oxygen concentration measurements (e.g. at the ocean floor) as occurs in FIG. 10c.

Video camera 32, see FIG. 1, transmits images of the ocean floor below to an operator who locates an appropriate landing site while the benthic flux sampling device is lowered as shown in FIG. 3b. When the water body floor is visible, and is considered to be adequate for landing device 10, the operator raises the benthic flux sampling device from between two to four meters above the water body floor. Benthic flux sampling device 10 is then released and free falls to the ocean floor under its own weight.

The weight and downward momentum of device 10 cause the knife edge periphery 90 of container 16 to pierce the sedimentary surface of the ocean floor. Thus, a seal between periphery 90 and the ocean floor is formed when benthic flux sampling device is positioned on the ocean floor as depicted in FIG. 10c. It can be appreciated that skirt 92 will contact the sedimentary surface of the ocean floor to limit the extent that periphery 90 pierces the ocean floor and to support device 10. Feet 64 of frame 12 also contact the ocean floor and function to support benthic flux sampling device 10 and container 16 an appropriate distance above the ocean floor without unduly disturbing sediment on the ocean floor during deployment. In this way, a sealing arrangement between container 16 and the water body floor is optimized and sedimentary disturbance is minimized.

After successful landing as shown in FIG. 10c, sampling procedures are initiated. The initial functions such as the closure of lid 18 and the initiation of operation of flow-through sensor system 26 are controlled by control unit 20 and may be monitored by video camera 32. Control unit 20 activates sensor system 26 and engages pump 118 which draws fluid initially from surrounding water and during sampling from container 16 through sensor system inlet 130 ,see FIG. 2 and FIG. 3. As fluid flows though sensor system 26, data is gathered periodically by the various sensors including oxygen sensor 136. Gathered data is transmitted through sensor cable 134 and oxygen sensor cable 162 to control unit 20 and recorded. During sampling the fluid is returned to container 16 through sensor system outlet 132 and helical diffuser 94 to simulate fluid flow under natural conditions and preserve the integrity of the sampling process.

Oxygen sensor 136 makes a series of ambient oxygen level measurements near the ocean floor before the closure of lid 18. More specifically, a specified number of initial measurements made by oxygen sensor 136 are communicated to the control unit, averaged and recorded. Control unit 20 then establishes maximum and minimum allowable oxygen levels based on a user specified, predetermined range about the average (ambient) concentration level.

Lid 18 is closed when control unit 20 initiates and transmits a signal along lid control line 126 to lid release 73 and causes release bar 128 to retract to disconnect from the recess in lid release hook 71, see FIG. 3. When lid release hook 71 is retracted and no longer holds lid 18 open that lid 18 will pivot about lid hinges 74 as lid 18 is pulled downward by gravity into a closed position as shown in FIG. 3.

The sampling process commences in response to a predetermined signal from control unit 20 through valve control line 114 to an individual sample valve 116. An individual sample valve 116 opens and allows a volume of fluid to pass from container 16 through supply line 106, past valve 116, through sample line 112 and into a sample bottle 22. Bottle 22 vents through vent line 110 and check valve 28. It can be appreciated that fluid is drawn from container 16 into a particular bottle 22 by the hydrostatic pressure difference between check valves 28 which mounted on the upper portion of frame arms 56 and base 14 where container 16 and sample bottles 22 are mounted.

The sampling process repeats ten times so that ten samples are obtained over a predetermined period in accordance with a predetermined sampling routine to validate a determination of the benthic flux measurements of substances of interest. From the series of samples, the benthic flux rate of toxins may be determined later in a laboratory.

Throughout the sampling process, the oxygenation system 30 maintains ambient oxygen levels within the container 16. Specifically, the control unit 20 continually monitors the oxygen sensor 136 and thus, the oxygen concentration in the sample which is isolated in container 16, see FIG. 9b. If the oxygen concentration drops below the minimum allowable level, the control unit initiates a signal, opening control valve 166, pressurizing the oxygenation system and the oxygen dispenser (e.g. oxygen diffuser), and dispensing oxygen into the sample chamber. When the oxygen concentration reaches the maximum allowable level, a second signal is initiated and transmitted by the control unit to the control valve which closes in response. The oxygen diffuser depressurizes and oxygen concentrations within fluid held in the chamber 17 begin to drop. This sequence is repeated over the course of the sampling process to maintain oxygen concentrations near ambient in the sample.

Retrieval of the benthic flux sampling device is shown in FIGS. 10d through 10g. A hydrophone is lowered into the water and emits an acoustic signal, see FIG. 10d. In response, acoustic release 68 causes buoy to be released from frame 12 and buoy 36 floats to the ocean surface, see FIG. 10e. Retrieval hook 66 is grasped by an operator, buoy 36 is pulled into the boat and retrieval line 40 is hoisted toward the ocean surface, note FIG. 10f. A relatively stronger air lift line may be attached to release padeye 46 for lifting device 10 through the water-air interface and into the boat, see FIG. 10g.

Once device 10 is retrieved, recorded sensor data is uploaded into the operator's computer. The captured fluid samples are analyzed at a later time in a well equipped laboratory. It cam be appreciated that credible analysis results are obtained because the samples are not disturbed and efforts are taken to maintain sample integrity such as oxygenation, maintenance of fluid flow, large number of samples (ten) and reduction of sedimentary disturbance during deployment and minimization of self-contamination for example. Accordingly, toxin levels found in the samples are reflective of natural conditions and flux rates can be determined.

Referring once again to FIG. 9b a method 200 of maintaining a constant oxygen concentration in an isolated volume of fluid includes a determining 210 of oxygen concentration by measuring of an ambient oxygen concentration in an ambient fluid and an isolated volume oxygen concentration in the isolated volume of fluid with an oxygen sensor. A preestablishing 220 of allowable maximum and minimum oxygen levels in the isolated volume may be made so that the oxygen concentration levels in the isolated volume substantially corresponds to the oxygen concentration levels in the ambient fluid. A continuing measuring 230 of the oxygen levels id the isolated volume of fluid is provided for by a monitoring 240 of the oxygen sensor with a control unit attached in electronic communication with the oxygen sensor so that a selectively dispensing 250 of oxygen into the isolated fluid with an oxygenation system attached to the control unit can be done by electronically activating the oxygenation system with the control unit to maintain a constant isolated volume oxygen concentration in the isolated volume of fluid that substantially corresponds to the ambient oxygen concentration in the ambient fluid or at least between the allowable maximum and minimum levels with the oxygenation system which has an oxygen storage tank, a pressure regulator, an oxygen control valve and an oxygen dispenser.

The determining of oxygen concentration of the ambient fluid and isolated volume of fluid may include a first determining of the ambient oxygen concentration of the ambient fluid by a measuring and averaging of an initial series of ambient oxygen concentration measurements with the ambient oxygen concentration equaling the average of the initial series of oxygen concentration measurements and a measuring and averaging of a series of isolated volume oxygen concentration measurements with the isolated volume oxygen concentration equaling the average of the series of isolated volume oxygen concentration measurements. Periodically measuring the isolated volume oxygen concentration in the isolated volume of fluid monitors oxygenation of the isolated volume of fluid.

As disclosed, the invention is capable of oxygenation of fluid to facilitate accurate sampling of benthic flux rates across a fluid boundary (i.e. the sediment at a water body floor). While the invention has been described with reference to a preferred embodiment thereof, as will be apparent to those skilled in the art, certain changes and modifications can be made without departing from the scope of the invention as defined by the following claims.

I claim

1. An apparatus for oxygenation of an isolated volume of fluid comprising:
    a container disposed to isolate said isolated volume from ambient water and air;
    a sensor system mounted on said apparatus in communication with said isolated volume of fluid to monitor oxygen concentrations thereof;
    an oxygenation system mounted on said apparatus in communication with said isolated volume of fluid to deliver oxygen thereto; and
    a control unit mounted on said apparatus in electronic communication with said sensor system and said oxygenation system to activate said oxygenation system when oxygen concentrations in said isolated volume of fluid fall below a predetermined minimum level and to deactivate said oxygenation system when oxygen concentrations in said isolated volume of fluid rise above a predetermined maximum level.

2. An apparatus according to claim 1 in which said oxygen sensor system includes a pump in fluid communication with a flow through oxygen sensor to pump said fluid past said oxygen sensor to measure dissolved oxygen concentrations in said fluid.

3. An apparatus according to claim 1 in which said oxygenation system includes an oxygen tank having a pressure regulator, said oxygen tank being connected in fluid communication through an oxygen supply line to an oxygen diffuser to deliver oxygen to said fluid.

4. An apparatus according to claim 3 in which said oxygen diffuser is an oxygen gas permeable, 50 meter long coil of 4 millimeter diameter, thin-walled teflon tube capable of holding and diffusing oxygen pressurized at pressures including 200 psi.

5. An apparatus according to claim 3 in which said oxygenation system includes an oxygen control valve attached between a regulator and said diffuser, said oxygen control valve being in electronic communication with said control unit to selectively regulate the flow of oxygen through said oxygen supply line in response to a signal generated by said control unit.

6. An apparatus according to claim 5 in which said control unit activates said oxygenation system by opening said oxygen control valve when oxygen concentrations in said fluid fall below said predetermined minimum allowable level and deactivates said oxygenation system by closing said oxygen control valve when oxygen levels in said fluid rise above said predetermined maximum allowable level.

7. An apparatus for maintaining ambient oxygen concentrations in a volume of water comprising:
    a container to isolate said volume of water near an ocean floor;
    an oxygen sensor system mounted on said container in fluid communication with ambient water and the isolated volume of water to provide initial ambient oxygen concentration level measurements in surrounding water and to provide periodic oxygen concentration measurements in said isolated volume of water in said container;
    a control unit in electronic communication with said oxygen sensor to continuously monitor said initial ambient oxygen concentration measurements and said periodic oxygen concentration measurements of said oxygen sensor; and
    an oxygenation system in electronic communication with said control unit and in fluid communication with said container, said oxygenation system includes an oxygen storage tank connected to a pressure regulator in fluid communication with an oxygen control valve and an oxygen diffuser to automatically deliver oxygen to said isolated volume of water in said container to maintain a oxygen concentration level within said container that is substantially the same as said ambient oxygen concentration level.

8. An apparatus according to claim 7 in which said oxygen diffuser is an oxygen gas permeable, 50 meter long coil of 4 millimeter diameter, thin-walled teflon tube capable of holding and diffusing oxygen pressurized at pressures including 200 psi.

9. An apparatus according to claim 8 in which said pressure regulator is an adjustable first stage regulator to allow selective regulation of pressure within said oxygenation system and dispense oxygen at a rate dependent on said regulated pressure.

10. An apparatus according to claim 9 in which said control unit is electronically connected with said oxygenation system through an oxygen valve control cable which is electronically connected to said oxygen control valve, said control unit activates said oxygenation system by dispatching an electronic signal to open said control valve, to pressurize said oxygenation system and to permit oxygen delivery from said oxygen storage tank into said container.

11. An apparatus according to claim 10 in which said control unit activates said oxygenation system only when at least one of said periodic oxygen concentration measurements in said volume of water falls below a minimum allowable value and said control unit deactivates said oxygenation system by closing said oxygen control valve when at least one of said periodic oxygen concentration measurements in said volume of water rises above a maximum allowable value.

12. An apparatus according to claim 11 in which said oxygenation system communicates with said oxygen sensor through an oxygen sensor cable and said control unit to monitor and average a series of said initial oxygen concentration measurements, wherein said ambient oxygen concentration is determined from said average.

13. An apparatus according to claim 12 in which said oxygen control valve is a 12 volt, latching solenoid valve.

14. A method for maintaining a constant oxygen concentration in an isolated volume of fluid comprising:
    measuring an ambient oxygen concentration in ambient fluid and an isolated volume oxygen concentration in said isolated volume of fluid with an oxygen sensor;

monitoring said oxygen sensor with a control unit attached in electronic communication with said oxygen sensor; and selectively dispensing oxygen into said isolated fluid with an oxygenation system attached to said control unit by electronically activating said oxygenation system with said control unit to maintain a constant said isolated volume oxygen concentration in said isolated volume of fluid that substantially corresponds to said ambient oxygen concentration in said ambient fluid, said oxygenation system having an oxygen storage tank, a pressure regulator, an oxygen control valve and an oxygen dispenser.

15. A method according to claim 14 in which said oxygen dispenser is an oxygen gas permeable, 50 meter long coil of 4 millimeter diameter, thin-walled teflon tube capable of holding and diffusing oxygen so that the rate at which oxygen is dispensed depends-on the pressure at which oxygen is held within said tube.

16. A method as recited in claim 14, wherein said oxygenation system includes an oxygen bleed valve to allow oxygen to escape 7hen pressure within said oxygenation system exceeds appropriate levels.

17. A method as recited in claim 14, in which said oxygenation system maintains constant said isolated volume oxygen consentration without contamination to said isolated volume.

18. A method according to claim 14 further comprising:

first determining said ambient oxygen concentration of said ambient fluid by measuring and averaging an initial series of ambient oxygen concentration measurements, said ambient oxygen concentration equaling the average of said initial series of oxygen concentration measurements; and periodically repeating the step of measuring said isolated volume oxygen concentration in said isolated volume of fluid.

19. A method according to 18 in which said oxygen control valve is capable of actuation between an open and a closed position to respectively pressurize and de-pressurize said oxygen dispenser.

20. A method according to claim 19 in which said oxygen control valve is a twelve volt, latching solenoid valve and said control unit functions to electronically open and close said oxygen control valve to maintain said ambient oxygen level.

21. A method according to claim 19 in which said pressure regulator is a first stage regulator which is adjustable to maintain a constant pressure within said oxygen dispenser when said oxygen control valve is in said open position to dispense oxygen at a constant rate.

22. A method according to claim 21 in which said constant rate equals the rate at which oxygen is required to maintain said ambient oxygen level so that the step of dispensing oxygen occurs only once.

* * * * *